(12) United States Patent
Imoto et al.

(10) Patent No.: US 6,900,202 B2
(45) Date of Patent: May 31, 2005

(54) DI-SUBSTITUTED IMINEHETEROCYCLIC COMPOUNDS

(75) Inventors: Masahiro Imoto, Tatebayashi (JP); Tatsuya Iwanami, Ashikaga (JP); Minako Akabane, Ibaraki (JP); Yoshihiro Tani, Ibaraki (JP)

(73) Assignee: Daiichi Suntory Pharma Co., Ltd., Tokyo (JP)

(*) Notice: Subject to any disclaimer, the term of this patent is extended or adjusted under 35 U.S.C. 154(b) by 41 days.

(21) Appl. No.: 09/979,162

(22) PCT Filed: Mar. 21, 2001

(86) PCT No.: PCT/JP01/02208

§ 371 (c)(1),
(2), (4) Date: Nov. 20, 2001

(87) PCT Pub. No.: WO01/70733

PCT Pub. Date: Sep. 27, 2001

(65) Prior Publication Data

US 2003/0078259 A1 Apr. 24, 2003

(30) Foreign Application Priority Data

Mar. 21, 2000 (JP) .............................. 2000-078966

(51) Int. Cl.[7] ............... C07D 411/02; C07D 411/14; C07D 413/02; A61K 31/5355; A61K 31/422
(52) U.S. Cl. ................. 514/228.8; 514/377; 544/96; 548/234
(58) Field of Search ................ 544/96; 548/234; 514/228.8, 377

(56) References Cited

U.S. PATENT DOCUMENTS

| | | | |
|---|---|---|---|
| 3,640,952 A | * 2/1972 | Metzger et al. | 260/45.8 |
| 3,686,199 A | * 8/1972 | Wollweber et al. | 260/307 F |
| 3,787,575 A | * 1/1974 | Wollweber et al. | 424/272 |
| 4,046,909 A | 9/1977 | Rasmussen et al. | 424/274 |
| 4,139,537 A | 2/1979 | Diamond et al. | 546/309 |
| 4,414,211 A | 11/1983 | Rasmussen | 424/246 |
| 4,468,403 A | 8/1984 | Knaus et al. | 546/193 |
| 5,922,881 A | * 7/1999 | Assmann et al. | 548/124 |

FOREIGN PATENT DOCUMENTS

| | | |
|---|---|---|
| EP | 0011963 | 6/1980 |
| EP | 0018134 | 10/1980 |
| EP | 0451651 | 12/1991 |
| EP | 0432600 | 10/1993 |
| WO | WO-89 04595 A | * 6/1989 |
| WO | 99/62505 | 12/1999 |

OTHER PUBLICATIONS

Clementi et al., European Journal of Pharmacology 393, 3–10, 2000.*

* cited by examiner

*Primary Examiner*—Venkataraman Balasubramanian
(74) *Attorney, Agent, or Firm*—Crowell & Moring LLP

(57) ABSTRACT

There is provided di-substituted iminoheterocyclic compounds of the following formula (I):

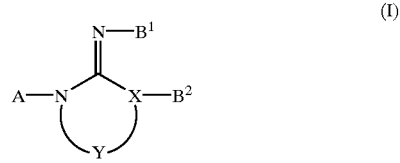

in which,
A is optionally substituted alkyl group, optionally substituted aryl group or optionally substituted heterocyclic group;
X is oxygen atom, sulfur atom, carbon atom or nitrogen atom;
the group —X—Y— represents optionally substituted alkylene or cyclic alkenylene bond; and
$B^1$ and $B^2$ are, hydrogen atom, optionally substituted alkyl group, optionally substituted aryl group or optionally substituted heterocyclic group, independent from each other,
or a pharmaceutically acceptable salt thereof.

These compounds have good affinity for α4β2 nicotinic acetylcholine receptors and activate the same to thereby exert a preventive or therapeutic effect on cerebral dysfunction.

5 Claims, No Drawings

DI-SUBSTITUTED IMINEHETEROCYCLIC COMPOUNDS

TECHNICAL FIELD

The present invention relates to compounds showing affinity for nicotinic acetylcholine receptors and activating the same. The compounds of the present invention are useful for preventing or treating of neurodegenerative diseases such as Alzheimer's disease and Parkinson's disease, dementia such as cerebrovascular dementia, motor ataxia such as Tourette's syndrome, neurological disease such as chronic cerebral infarction, neuropathy and mental disorder such as anxiety and schizophrenia and cerebral dysfunction caused by cerebral injury.

BACKGROUND ART

It has been widely known that nicotine exerts a wide variety of pharmacological effects. These include, for example, cholinergic nervous activation as the effect on central nervous systems such as facilitation of acetylcholine release [De sarno P. & Giacobini E., J. Neurosci. Res., 22, 194–200 (1984)], and further, activation effect on monoaminergic nervous systems [Levin E. D. & Simon B. B., Psychopharmacology, 138, 217–230 (1998)].

It has been also reported that nicotine possesses lots of very useful cerebral function improving effects such as increasing cerebral blood flow and glucose uptake rate in brain [Decker M. W. et al., Life Sci., 56, 545–570 (1995)].

It has been further reported that nicotine inhibits amyloid formation of β-peptides which is believed to be the cause of neuronal cell death during Alzheimer's disease [Salomon A. R. et al., Biochemistry, 35, 13568–13578 (1996)], and have cell protective effects on neuronal cell death induced by β-amyloid (Aβ) [Kihara T. et al., Ann. Neurol., 42, 156–163 (1997)]. Recent studies suggest the possibility of nicotine being a remedy for the inflammatory colitis [Sandborn W. J. et al., Ann. Intern. Med., 126, 364 (1997)].

On the other hand, it is acknowledged that in the patients of Alzheimer's disease, the degeneration of acetylcholinergic neurons known to be one of the important nervous systems responsible for cognition such as attention, learning, memory and recognition, is altered and thus nicotinic acetylcholine receptors in the cerebral cortex and hippocampus are drastically decreased [Nordberg A. et al., J. Neurosci. Res., 31, 103–111 (1992)].

It is reported the possibility of the useful treatment for Alzheimer's disease by activating nicotinic acetylcholine receptors to be recovered the acetylcholine nervous systems mechanism by agonists or modulators of nicotinic acetylcholine receptors [Newhouse P. A. et al., Psychopharmacology, 95, 171–175 (1988)].

The nicotinic acetylcholine receptors belong to the ion channel neurotransmitter receptors composed of five subunits. That is, agonists such as acetylcholine, nicotine and the like are bound to receptors to activate and open the channels thereof, thus causing the influx of cationic ion such as sodium ion from extracellular to result the cell excitation [Galzi J. L. & Changeux J. P., Neuropharmacology, 34, 563–582 (1995)]. The aforementioned agonists such as acetylcholine, nicotine and the like show its effect by binding to the specific site existing in α subunit so-called agonist binding site.

It is known, on the other hand, that compounds such as galantamine and so on which activate cells by potentiating the effects of acetylcholine, have no agonist effect at nicotinic acetylcholine receptors directly. These compounds show their effects through allosteric site which is clearly different from the agonist binding sites [Schrattenholz A. et al., Mol. Pharmacol., 49, 1–6 (1996)].

Mentioned above, compounds capable to activate nicotinic acetylcholine receptors indirectly are called modulators and it is expected to be the practical medicines for treatment of the various neurological diseases [Lin N. -H & Meyer M. D., Exp. Opin. Thr. Patents, 8, 991–1015 (1998)].

The terms "agonists" and "modulators" are used in these definitions in the present specification.

The nicotinic acetylcholine receptors are believed to participate not only in Alzheimer's disease, but also in neurodegenerative diseases such as Parkinson's disease, and many of the neuroses and psychoses such as dementia, anxiety, schizophrenia and so on [Barrantes F. J., in The Nicotic Acetylcholine Receptor, ed. Barrantes F. J., Springer, 1997, p175–212; Lena C. & Changeux J. -P., J. Physiol. (Paris), 92, 63–74 (1998)].

Especially, since it is known that cerebral blood flow of the patients suffering from cerebrovascular dementia caused by cerebral infarction is decreased [Takagi Shigeharu, Gendal Iryo, 28, 1157–1160 (1996); Tachibana H. et al., J. Gerontol., 39, 415–423 (1984)], there seems to be the possibility of agonists of nicotinic acetylcholine receptors or the modulators possessing cerebral blood flow increasing effect to be applied to the medicines in this area of treatment. Furthermore, recent study revealed that agonists of nicotinic acetylcholine receptors and the modulators thereof show analgesic activities [Bannon A. W. et al., Science, 279, 77–81 (1998)].

Nicotine itself surely affects as the agonist of nicotinic acetylcholine receptors. For example, after administration of nicotine to the patients of Alzheimer's disease, the recoveries of their attention or the short-term memory were observed, and also the symptoms of their disease were improved [Newhouse P. A. et al., Drugs & Aging, 11, 206–228 (1997)]. Nevertheless, nicotine also possesses disadvantages such as widely recognized addiction, as well as low bioavailability and severe side effects to the cardiovascular systems.

Therefore, there have been great expectation to develop nicotinic acetylcholine receptors agonists or modulators as medicines in place of nicotine which has no addiction, high bioavailability, and less side effects on cardiovascular systems [Maelicke A. & Albuquerque E. X., Drug Discovery Today, 1, 53–59 (1996); Holladay M. W. et al., J. Med. Chem., 40, 4169–4194 (1997)].

There are some subtypes known as the nicotinic acetylcholine receptors [Shacka J. J. & Robinson S. E. T, Med. Chem. Res., 1996, 444–464], and mainly α4β2 subtype receptors exist in central nervous systems. Furthermore, there exist α1β1γδ (or α1β1εδ) subtype receptors in the neuromuscular junction of motor neurons, and α3β4 subtype receptors in ganglion of autonomic nervous systems and adrenal.

The activation of the cholinergic nervous systems and increasing effect of cerebral blood flow are believed to occur though α4β2 subtype receptors in central nervous systems, and above mentioned effects of nicotine on cardiovascular system are induced by affecting receptor subtypes exist in peripheral nervous system.

Therefore, it may be extremely useful as medicines having no side effects to develop compounds which have no affinity at α1β1γδ subtype nor α3β4 subtype receptors, but selectively affects α4β2 subtype receptors.

In these circumstances, there have been many proposals to develop selective agonists or modulators at nicotinic acetylcholine receptors of central nervous system as practical medicines. These include, for example, the compound such as ABT-418 [Arneric S. P. et al., J. Pharmacol. Exp. Ther., 270, 310–318 (1994); Decker M. W. et al., J. Pharmacol. Exp. Ther., 270, 319–328 (1994)], ABT-089 [Sullivan J. P. et al., J. Pharmacol. Exp. Ther., 283, 235–246 (1997); Decker M. W. et al., J. Pharmacol. Exp. Ther., 283, 247–258 (1997)], GTS-21 [Arendash G. W. et al., Brain Res., 674, 252–259 (1995); Briggs C. A. et al., Pharmacol. Biochem. Behav., 57, 231–241 (1997)], RJR-2403 [Bencherif M. et al., J. Pharmacol. Exp. Ther., 279, 1413–1421 (1996); Lippiello P. M. et al., J. Pharmacol. Exp. Ther., 279, 1422–1429 (1996)], SIB-1508Y [Cosford N. D. P. et al., J. Med. Chem., 39, 3235–3237 (1996); Lloyd. G. K. et al. Life Sci., 1601–1606 (1995)], SIB-1553A [Lloyd. G. K. et al., Life Sci., 62, 1601–1606 (1995)] and so on.

In European Patent Publication EP679397-A2, substituted amine derivatives represented by the following formula were proposed for the medicines for prevention and treatment of cerebral dysfunction.

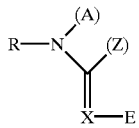

in which,

R represents hydrogen, optionally substituted acyl, alkyl, aryl, aralkyl, heteroaryl or heteroarylalkyl radicals;

A represents a monofunctional group of the hydrogen, acyl, alkyl or aryl series or represents a bi-functional group which is linked to the radical Z;

E represents an electron-withdrawing radical;

X represents the —CH= or =N— radicals, it being possible for the —CH= radical to be linked to the Z radical instead of an H atom;

Z represents a monofunctional group of the alkyl, —O—R, —S— R or —NR$_2$ series or represents a bi-functional group which is linked to the A radical or the X radical.

However, in the compounds disclosed in said patent publication, the E radical is restricted to the electron-withdrawing radical, and therefore, these compounds are clearly different from the compounds disclosed by the present patent application. Furthermore, there is no description in the above-mentioned patent publication that these compounds can selectively activate α4β2 nicotinic acetylcholine receptors.

On the other hand, "imidacloprid", as a pesticide, is known to have the similar skeleton as the compounds of the present invention. It is confirmed that the imidacloprid electrophysiologically affects as partial agonist at nicotinic acetylcholine receptors of PC12 cell [Nagata K. et al., J. Pharmacol. Exp. Ther., 285, 731–738 (1998)], and imidacloprid itself or its metabolites and their analogues possess affinity to the nicotinic acetylcholine receptors in mouse brain [Lee Chao S. & Casida E., Pestic. Biochem. Physiol., 58, 77–88 (1997); Tomizawa T. & Casida J. E., J. Pharmacol., 127, 115–122 (1999); Latli B. et al., J. Med. Chem., 42, 2227–2234 (1999)], however, there is no report of the imidacloprid derivatives selectively activating α4β2 nicotinic acetylcholine receptors.

Japanese Laid-open Patent Publication Number Hei 10-226684 disclosed [N-(pyridinylmethyl)heterocyclic]ylideneamine compounds represented by the following formula, pharmaceutically acceptable salts and prodrugs thereof.

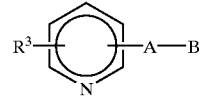

in which,

A represents the —CH(R)—;

R$^3$ represents a hydrogen atom or an optionally substituted C$_1$-C$_6$ alkyl; and B represents the group of the following formula:

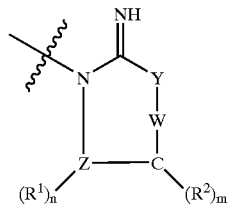

Nevertheless, among the compounds disclosed in said patent publication, the imino group and radical Y in the compounds have no substituent, and therefore, these compounds are clearly different from the compounds of the present invention. It is disclosed that aforementioned compounds possess weak affinity to nicotinic receptors; however, there is no disclosure that these compounds have selective activating effect at α4β2 nicotinic acetylcholine receptors of central nervous systems and act as agonists or modulators of nicotinic acetylcholine receptors.

As mentioned above, there had been many attempts to develop agonists or modulators selectively activating α4β2 nicotinic acetylcholine receptors of central nervous systems via oral administration, but none were satisfactory.

DISCLOSURE OF THE INVENTION

Therefore, the present invention provides therapeutic or preventing agents for treatment of diseases which may be prevented or cured by activating nicotinic acetylcholine receptors, having the capabilities of binding selectively with α4β2 nicotinic acetylcholine receptor of central nervous systems, and having no undesirable side effects in cardiovascular systems such as hypertension or tachycardia.

More specifically, the present invention provides medicaments for preventing or treating various diseases, which may be prevented or cured by activating nicotinic acetylcholine receptors, such as dementia, senile dementia, presenile dementia, Alzheimer's disease, Parkinson's disease, cerebrovascular dementia, AIDS-related dementia, dementia in Down's syndrome, Tourette's syndrome, neurosis in chronic cerebral infarction, cerebral dysfunction caused by cerebral injury, anxiety, schizophrenia, depression, Huntington's disease, pain and so on.

Through extensive investigations of researching compounds having the capabilities of binding selectively with α4β2 nicotinic acetylcholine receptors of central nervous systems, the present inventors discovered that the compounds represented by the formula (I) mentioned below and pharmaceutically acceptable salts thereof possess high affinity for nicotinic acetylcholine receptors in central nervous systems, and activate said receptors as agonists or modulators.

Accordingly, as one aspect of the present invention, it is provided di-substituted iminoheterocyclic compounds represented by the following formula (I):

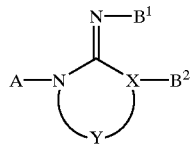
(I)

wherein:
A is optionally substituted alkyl group; optionally substituted aryl group; or optionally substituted heterocyclic group;
X is oxygen atom; sulfur atom; carbon atom; or nitrogen atom; and
Y, $B^1$ and $B^2$ are, (1) in the case of X is oxygen atom, group —Y—X— is —$CH_2$—$CH_2$—O— or —$CH_2$—$CH_2$—$CH_2$—O—; $B^1$ is optionally substituted alkyl group; optionally substituted aryl group; or optionally substituted heterocyclic group; and $B^2$ is null;

(2) in the case of X is sulfur atom, group —Y—X— is —$CH_2$—$CH_2$—S— or —$C(R^1)$=$C(R^2)$—S— (in which, $R^1$ and $R^2$ are hydrogen atom; halogen atom; optionally substituted alkyl group; optionally substituted aryl group; or optionally substituted heterocyclic group); $B^1$ is optionally substituted alkyl group; optionally substituted aryl group; or optionally substituted heterocyclic group; and B2 is null;

(3) in the case of X is carbon atom, group —Y—X— is —CH=$C(R^3)$—$C(R^4)$=CH—, —$CH(R^5)$—$CH_2$—$CH_2$— or —N=$C(R^6)$—$C(R^7)$=CH— (in which, $R^3$, $R^4$, $R^5$, $R^6$ and $R^7$ are hydrogen atom; halogen atom; optionally substituted alkyl group; optionally substituted aryl group; or optionally substituted heterocyclic group); $B^1$ is optionally substituted alkyl group; optionally substituted aryl group; or optionally substituted heterocyclic group; and $B^2$ is hydrogen atom; and, (4) in the case of X is nitrogen atom, group —Y—X— is —$CH_2$—$CH_2$—$N(B^2)$—, —$C(R^8)$=$C(R^9)$—$N(B^2)$—, —$CH_2$—$CH_2$—$CH_2$—$N(B^2)$— or —CH=$C(R^{10})$—C$(R^{11})$=N— (in which, $R^8$, $R^9$, $R^{10}$ and $R^{11}$ are hydrogen atom; halogen atom; optionally substituted alkyl group; optionally substituted aryl group; or optionally substituted heterocyclic group); one of $B^1$ and $B^2$ is hydrogen atom and other is optionally substituted alkyl group; optionally substituted aryl group; or optionally substituted heterocyclic group,
or pharmaceutically acceptable salts thereof.

Still another aspect of the present invention, it is provided activator agents for α4β2 nicotinic acetylcholine receptors containing di-substituted iminoheterocyclic compounds of the formula (I) or pharmaceutically acceptable salt thereof as active ingredients.

As still further aspect of the present invention, it is provided that the use of di-substituted iminoheterocyclic compounds of the formula (I) or pharmaceutically acceptable salt thereof for treating or preventing of cerebral circulation disease, neurodegenerative disease and the like.

BEST MODE FOR CARRYING OUT THE INVENTION

Examples of the pharmaceutically acceptable salt include an inorganic acid salt such as hydrochloric acid salt, hydrobromic acid salt, sulfuric acid salt, phosphoric acid salt, periodic acid salt and the like, and an organic acid salt such as fumaric acid salt, maleic acid salt, oxalic acid salt, citric acid salt, tartaric acid salt, malic acid salt, lactic acid salt, succinic acid salt, benzoic acid salt, methanesulfonic acid salt, p-toluenesulfonic acid salt and the like.

The group represented by "A" in the compound of formula (I) is optionally substituted alkyl group, optionally substituted aryl group or optionally substituted heterocyclic group, and preferable examples of said optionally substituted alkyl group includes methyl, ethyl, benzyl, 4-chlorobenzyl, 3-pyridylmethyl, (6-chloro-3-pyridyl)methyl, (6-methyl-3-pyridyl)methyl, (5,6-di-chloro-3-pyridyl)methyl, 2-(6-chloro-3-pyridyl)ethyl and the like.

The preferable examples of aryl group may include phenyl, naphthyl and the like. Suitable substituent of substituted aryl group may include $C_1$–$C_4$ lower alkyl, halogen atom and the like, and therefore, examples of said substituted aryl group include methylphenyl, chlorophenyl, dichloropheny and the like.

The term "heterocyclic group" represented by "A" may be 5 or 6 membered heterocyclic group containing the same or different 1 to 3 hetero atom(s) such as sulfur, nitrogen, oxygen atom(s), and examples include thiophene, furan, pyran, pyrrole, pyrazole, pyridine, pyrimidine, pyrazine, pyridazine, imidazole, oxazole, isoxazole, thiazole, isothiazole, quinoline, isoquinoline, tetrahydropyrimidine and the like.

Suitable substituent of substituted heterocyclic group may include $C_1$–$C_4$ lower alkyl, halogen atom and the like, and therefore, examples of said substituted heterocyclic group may be 2-methylpyridine, 2-chloropyridine, 2-fluoropyridine, 2-bromopyridine, 3-bromopyridine, 2,3-dichloropyridine, 2-chlorothiazole, 3-methylisoxazole, and the like.

The group represented by "$B^1$" in the compound of formula (I) is hydrogen atom, optionally substituted alkyl group, optionally substituted aryl group or optionally substituted heterocyclic group, and preferable examples of said optionally substituted alkyl group include methyl, ethyl, benzyl, 4-chlorobenzyl, 3-pyridylmethyl, (6-chloro-3-pyridyl)methyl, (6-methyl-3-pyridyl)methyl, (5,6-dichloro-3-pyridyl)methyl, 2-(6-chloro-3-pyridyl)ethyl and the like.

The preferable examples of aryl group may include phenyl, naphthyl and the like. Suitable substituent of substituted aryl group may include $C_1$–$C_4$ lower alkyl, halogen atom and the like, and therefore, examples of said substituted aryl group include methylphenyl, chlorophenyl, dichloropheny and the like.

The term "heterocyclic group" represented by "$B^1$" may be 5 or 6 membered heterocyclic group containing the same or different 1 to 3 hetero atom(s) such as sulfur, nitrogen, oxygen atom(s), and examples include thiophene, furan, pyran, pyrrole, pyrazole, pyridine, pyrimidine, pyrazine, pyridazine, imidazole, oxazole, isoxazole, thiazole, isothiazole, quinoline, isoquinoline, tetrahydropyrimidine and the like.

Suitable substituent of substituted heterocyclic group may include $C_1$–$C_4$ lower alkyl, halogen atom and the like, and therefore, examples of said substituted heterocyclic group may be 2-methylpyridine, 2-chloropyridine, 2-fluoropyridine, 2-bromopyridine, 3-bromopyridine, 2,3-dichloropyridine, 2-chlorothiazole, 3-methylisoxazole, and the like.

The group represented by "X" in the compound of formula (I) stands for oxygen atom, sulfur atom, carbon atom or nitrogen atom, and the "X" is combined with "Y" to constitute the partial component represented by "—Y—X—", which has follow meanings.

(1) in the case of "X" is oxygen atom, the term "—Y—X—" is —CH$_2$—CH$_2$—O— or —CH$_2$—CH$_2$—CH$_2$—O—;

(2) in the case of "X" is sulfur atom, the term "—Y—X—" is —CH$_2$—CH$_2$—S— or —C(R$^1$)=C(R$^2$)—S—,
(in which, R$^1$ and R$^2$ are hydrogen atom; halogen atom; optionally substituted alkyl group; optionally substituted aryl group; or optionally substituted heterocyclic group);

(3) in the case of "X" is carbon atom, the term "—Y—X—" is —CH=C(R$^3$)—C(R$^4$)=CH—, —CH(R$^5$)—CH$_2$—CH$_2$—CH$_2$— or —N=C(R$^6$)—C(R$^7$)=CH—,
(in which, R$^3$, R$^4$, R$^5$, R$^6$ and R$^7$ are hydrogen atom; halogen atom; optionally substituted alkyl group; optionally substituted aryl group; or optionally substituted heterocyclic group);

(4) in the case of "X" is nitrogen atom, the term "—Y—X—" is —CH$_2$—CH$_2$—N(B$^2$)—, —C(R$^8$)=C(R$^9$)—N(B$^2$)—, —CH$_2$—CH$_2$—CH$_2$—N(B$^2$)— or —CH=C(R$^{10}$)—C(R$^{11}$)=N—
(in which, R$^8$, R$^9$ R$^{10}$ and R$^{11}$ are hydrogen atom; halogen atom; optionally substituted alkyl group; optionally substituted aryl group; or optionally substituted heterocyclic group).

The term "halogen atom" represented by R$^1$, R$^2$, R$^3$, R$^4$, R$^5$, R$^6$, R$^7$, R$^8$, R$^9$, R$^{10}$ and R$^{11}$ may include fluorine, chlorine, bromine and iodine.

The term "optionally substituted alkyl group" may include methyl, ethyl, propyl, isopropyl, butyl, sec-butyl, tert-butyl and the like.

The term "optionally substituted aryl group" may be non-substituted phenyl group or phenyl group which is substituted by halogen atom, or C$_1$–C$_4$ lower alkyl such as methyl, ethyl and the like, and therefore, examples of substituted phenyl group may include methylphenyl, chlorophenyl, dichlorophenyl and the like.

The term "heterocyclic group" may be 5 or 6 membered heterocyclic group containing the same or different 1 to 3 hetero atom(s) such as sulfur, nitrogen, oxygen atom(s), and examples include thiophene, furan, pyran, pyrrole, pyrazole, pyridine, pyrimidine, pyrazine, pyridazine, imidazole, oxazole, isoxazole, thiazole, isothiazole, quinoline, isoquinoline, tetrahydro-pyrimidine and the like.

Suitable substituent of substituted heterocyclic group may include C$_1$–C$_4$ lower alkyl, halogen atom and the like, and therefore, examples of said substituted heterocyclic group may be 2-methylpyridine, 2-chloropyridine, 2-fluoropyridine, 2-bromopyridine, 3-bromopyridine, 2,3-dichloropyridine, 2-chlorothiazole, 3-methylisoxazole, and the like.

With respect to the group represented by "B$^2$" in the formula (I), in the case of "X" is oxygen atom or sulfur atom, the group "B$^2$" is null in the formula (I); and in the case of "X" is carbon atom, the group "B$^2$" donates hydrogen atom; and in the case of "X" is nitrogen atom, the group "B$^2$" donates optionally substituted alkyl group, optionally substituted aryl group or optionally substituted heterocyclic group.

Examples of optionally substituted alkyl group, optionally substituted aryl group and optionally substituted heterocyclic group are the same as defined in the case of the group "B$^1$". Only in the case of the group "B$^2$" is optionally substituted alkyl group, optionally substituted aryl group or optionally substituted heterocyclic group, the group "B$^1$" has to be hydrogen atom.

The following are examples of di-substituted iminoheterocyclic compounds of the formula (I).

3-(6-chloro-3-pyridyl)methyl-2-[(6-chloro-3-pyridyl)methyl]imino-thiazolidine;
3-(6-chloro-3-pyridyl)methyl-2-[(6-chloro-3-pyridyl)methyl]imino-3,4,5,6-tetrahydro-2H-1,3-oxazine;
1-(6-chloro-3-pyridyl)methyl-2-[(6-chloro-3-pyridyl)methyl]imino-1,2,3,4,5,6-hexahydropyrimidine;
1,3-bis[(6-chloro-3-pyridyl)methyl]-2-imino-1,2,3,4,5,6-hexahydropyrimidine;
1-(6-chloro-3-pyridyl)methyl-2-[(6-chloro-3-pyridyl)methyl]imino-1,2-dihydropyrimidine;
5-chloro-1-(6-chloro-3-pyridyl)methyl-2-[(6-chloro-3-pyridyl)-methyl]imino-1,2-dihydropyridine;
1-(6-chloro-3-pyridyl)methyl-2-[(6-chloro-3-pyridyl)methyl]imino-6-methylpiperidine;
3-(6-chloro-3-pyridyl)methyl-2-[(6-chloro-3-pyridyl)methyl]imino-2,3-dihydrothiazole;
3-(6-chloro-3-pyridyl)methyl-2-[(6-chloro-3-pyridyl)methyl]imino-4-methyl-2,3-dihydrothiazole;
1,3-bis[(6-chloro-3-pyridyl)methyl]-2-imino-2,3-dihydroimidazole;
3-(6-chloro-3-pyridyl)methyl-2-methyliminothiazolidine;
3-(6-chloro-3-pyridyl)methyl-2-phenylimino-2,3-dihydrothiazole;
1-(6-chloro-3-pyridyl)methyl-2-imino-3-methyl-2,3-dihydro-imidazole;
2-benzylimino-3-(6-chloro-3-pyridyl)methylthiazolidine;
3-(6-chloro-3-pyridyl)methyl-2-[2-(6-chloro-3-pyridyl)ethyl]-iminothiazolidine.

The di-substituted iminoheterocyclic compounds represented by the formula (I) of the present invention can be prepared in accordance with the various synthetic processes such as following Process 1 to 3.

In the following reaction schemes, the groups A, B$^1$, B$^2$, X and Y have the same meanings mentioned above, and n is an integer of 1 or 2.

Process 1:

In accordance with the following reaction scheme, the compound of the formula (II) is reacted with the compound of the formula (III) to obtain the intermediate compound represented by the formula (IV). Then, the resulting intermediate compound of the formula (IV) is further reacted with compound (V) or (VI) to obtain the compound of formula (I) of the present invention.

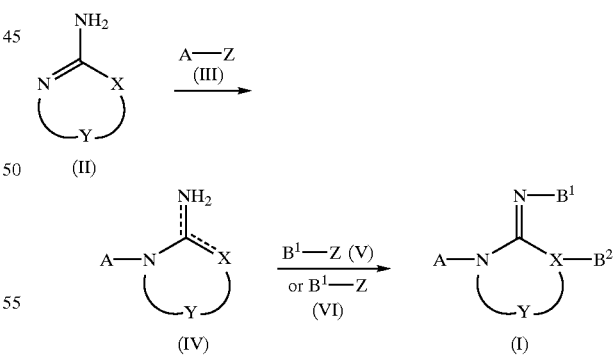

wherein, "Z" is leaving group which accelerates the reaction of A with nitrogen atoms of amino group or heterocyclic ring, such as halogen atom, p-toluenesulfonyloxy, methane-sufonyloxy, trifluoromethanesulfonyloxy, acyloxy, substituted acyloxy groups and so on. The dotted line represents either presence or absence of bond, and has following meanings in relation to number "n"; that is, in the case number "n" is 1, double bond is located between carbon atom of heterocyclic ring and exocyclic nitrogen atom, and so said nitrogen atom corresponds to imino group, and in another case number "n" is 2, double bond is located between carbon atom of heterocyclic ring and "X" which refers carbon or nitrogen atom, and then exocyclic nitrogen atom corresponds to amino group as substituent of heterocyclic ring.

The compound (II) to be used in this reaction can be commercially available or can be easily prepared from known compounds by using common methods.

The reaction of the compound (II) with the compound (III) to obtain the intermediate compound (IV), and the reaction of the resulting intermediate compound (IV) with the compound (V) or (VI) to obtain the compound (I) can be usually carried out in an appropriate solvent such as alcohol solvent, ketone solvent, nitrile solvent, ester solvent, amide solvent, hydrocarbon solvent and ether solvent or the mixture thereof in the presence of an organic base or an inorganic base if necessary, under the temperature ranging from −20° C. to the refluxing temperature of the solvent to be used.

The examples of alcohol solvent include methanol, ethanol, propanol, 2-propanol, 2-methyl-2-propanol and the like. The ketone solvent may include acetone, methyl ethyl ketone and the like. The nitrile solvent may include acetonitrile, propionitrile and so on, and the ester solvent may be ethyl acetate. The examples of amide solvent include N,N-dimethylformamide, N,N-dimethylacetamide, N-methylpyrrolidone, hexamethylphosphoramide and the like. The hydrocarbon solvent may include aromatic hydrocarbon such as benzene, toluene and the like, or aliphatic hydrocarbon such as pentane, hexane and the like. The examples of ether solvent may include diethyl ether, dimethoxyethane, tetrahydrofuran, 1,4-dioxane and the like.

Examples of the organic base to be used in the reaction may include triethylamine, collidine, lutidine, potassium tert-butoxide and the like, and the inorganic base may include potassium carbonate, sodium carbonate, sodium hydrogencarbonate, sodium hydroxide, potassium hydroxide and the like.

Process 2:

When the groups "A" and "B¹", or "A" and "B²" of the compound (I) are the same groups, said compound (I) can be obtained directly by the reaction of the compound (II) with excess amount of the compound (III), in accordance with the following reaction scheme.

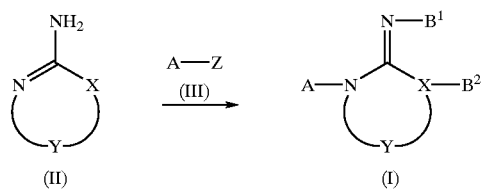

wherein, "Z" has the same meaning as above, and the groups "A" and "B¹", or "A" and "B²" are the same groups.

The reaction of the compound (II) with the compound (III) can be carried out in the same solvent in the presence of the same base as described in the Process 1 mentioned above. Furthermore, the reaction temperature and time are also the same as described in the Process 1 mentioned above.

Process 3:

When the group "X" of the compound (I) is sulfur atom, said compound (I) can be obtained by the reaction of the compound (VII) with the compound (III), in accordance with the following reaction scheme.

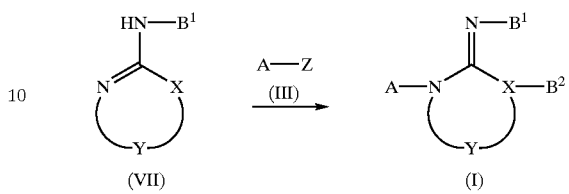

wherein, "X" is sulfur atom, "B²" is null, and "Z" has the same meaning as above.

The compound (VII) to be used in this reaction can be commercially available or can be easily prepared from known compounds by using common methods.

The reaction of the compound (VII) with the compound (III) can be carried out basically under the same reaction conditions of Process 1 or 2 above, that is, the solvent and the base used in the Process 1 and 2 can be used in this Process 3. Furthermore, the conditions of reaction temperature and time of the Process 1 and 2 can be also available in this Process 3.

The compound of formula (I) of the present invention thus obtained can be converted to a pharmaceutically acceptable salt with various kinds of the organic or inorganic acids mentioned above, if necessary. Furthermore, the compound (I) of the present invention can also be purified by the conventional manner, such as recrystallization, column chromatography and the like.

When the compounds of the formula (I) of the present invention exist in the isomer forms, each isomer per se is separated from each other by the conventional manner. Therefore, it is understood that each isomers per se, as well as the isomeric mixture, shall be included in the compounds of the present invention.

The compounds of formula (I) of the present invention bind selectively to nicotinic acetylcholine receptors in central nervous systems, and activate said receptors as agonists or modulators. Therefore, these compounds are useful as medicaments for preventing or treating various diseases, such as dementia, senile dementia, presenile dementia, Alzheimer's disease, Parkinson's disease, cerebrovascular dementia, AIDS-related dementia, dementia in Down's syndrome, Tourette's syndrome, neurosis in chronic cerebral infarction, cerebral dysfunction caused by cerebral injury, anxiety, schizophrenia, depression, Huntington's disease, pain and so on.

The compounds of formula (I) or a pharmaceutically acceptable salt thereof according to the present invention may be administered in the form of oral or parenteral formulations. The formulations for oral administration may include for example, tablets, capsules, granules, fine powders, syrups or the like; the formulations for parenteral administration may include, for example, injectable solutions or suspensions with distilled water for injection or other pharmaceutically acceptable solution, patches for transdermal application, sprays for nasally administration, depositories or the like.

These formulations may be formed by mixing with pharmaceutically acceptable carrier, excipient, sweetener, stabilizer and so on by the conventional procedures known per se to those skilled in the art in the field of pharmaceutical formulations.

Examples of pharmaceutically acceptable carrier or excipient include polyvinyl pyrrolidone, gum arabic, gelatin, sorbit, cyclodextrin, magnesium stearate, talc, polyethylene glycol, polyvinyl alcohol, silica, lactose, crystalline cellulose, sugar, starch, calcium phosphate, vegetable oil, carboxymethyl cellulose, hydroxypropyl cellulose, sodium lauryl sulfate, water, ethanol, glycerol, mannitol, syrup and the like.

The solutions for injection may be isotonic solution containing glucose and the like, and these solutions can be further contain an appropriate solubilizer such as polyethylene glycol or the like, buffer, stabilizer, preservative, antioxidant and so on.

These formulations can be administered to the human being and other mammalian animals, and the preferable administration route may include oral route, transdermic route, nasal route, rectal route, topical route or the like.

The administration dose may vary in a wide range with ages, weights, condition of patients, routes of administration or the like, and a usual recommended daily dose to adult patients for oral administration is within the range of approximately 0.001–1,000 mg/kg per body weight, preferably 0.01–100 mg/kg per body weight, and more preferably 0.1–10 mg/kg per body weight.

In the case of parenteral administration such as intravenous injections, a usual recommended daily dose is within the range of approximately 0.00001–10 mg/kg per body weight, preferably 0.0001–1 mg/kg per body weight, and more preferably 0.001–0.1 mg/kg per body weight, once or in three times per day.

The methods for evaluating the binding capabilities of the compounds against nicotinic acetylcholine receptors are different by subtypes of receptors. The binding capabilities of the compounds at $\alpha 4\beta 2$ nicotinic acetylcholine receptors are examined using rat brain membrane obtained from whole homogenized brain, and determining the inhibiting rate of the compounds against [$^3$H]-cytisine binding to said brain membrane. Furthermore, the binding capabilities of the compounds at $\alpha 1\beta 1\gamma\delta$ nicotinic acetylcholine receptors are examined using homogenized rat muscle, and determining the inhibiting rate of the compounds against [$^3$H]-$\alpha$-bungarotoxin binding to said muscle membrane.

The agonist effect in human $\alpha 4\beta 2$ subtype of nicotinic acetylcholine receptors are examined by using human nicotinic acetylcholine receptors prepared in oocytes of *Xenopus laevis*, which is injected with cRNA from the corresponding cloning cDNA of human $\alpha 4$ and $\beta 2$ subunits of nicotinic acetylcholine receptors, and to measure the expression of the electric response by adding the test compounds to perfusion solution by means of membrane potential holding method.

EXAMPLES

The present invention is illustrated in more detail by way of the following examples.

Example 1

Synthesis by the Process 1
2-Benzylimino-3-(6-chloro-3-pyridyl)methylthiazolidine
[Compound 14]

A mixture of 511 mg (5 mmol) of 2-amino-2-thiazoline and 1.03 g (5 mmol) of 5-bromomethyl-2-chloropyridine in 50 ml of acetonitrile was heated for 6 hours at 90° C. under refluxing. Then, the reaction mixture was cooled to the room temperature, and the solvent was removed under reduced pressure. The resulting residue was mixed with dichloromethane and saturated sodium hydrogen-carbonate aqueous solution, and the organic layer was separated. The water layer was extracted with dichloromethane, and combined organic layer was dried over magnesium sulfate. The solvent was removed under reduced pressure and the resulting residue was purified by aminopropyl-coated silica gel (Chromatorex NH-type; Fuji Silysia Chemical Ltd.) column chromatography (eluent; hexane:ethyl acetate=2:1) to give 623 mg (yield; 54.7%) of 3-(6-chloro-3-pyridyl)methyl-2-iminothiazolidine as yellow oil and 173 mg (yield; 7.4%) of 3-(6-chloro-3-pyridyl)methyl-2-[(6-chloro-3-pyridyl)methyl]iminothiazolidine as yellow oil.

Then, a mixture of 228 mg (1 mmol) of 3-(6-chloro-3-pyridyl)methyl-2-iminothiazolidine, 180 mg (1.05 mmol) of benzylbromide and 276 mg (2 mmol) of anhydrous potassium carbonate in 10 ml of acetonitrile was heated for 3 hours at 90° C. under refluxing. After the reaction mixture was cooled to the room temperature, the solvent was removed under reduced pressure. The resulting residue was mixed with dichloromethane and saturated sodium hydrogen carbonate aqueous solution, and the organic layer was separated. The water layer was extracted with dichloromethane, and combined organic layer was dried over magnesium sulfate. The solvent was removed under reduced pressure and the resulting residue was purified by aminopropyl-coated silica gel (Chromatorex NH-type; Fuji Silysia Chemical Ltd.) column chromatography (eluent; hexane:ethyl acetate=2:1) to give 217 mg (yield; 68.3%) of 2-benzylimino-3-(6-chloro-3-pyridyl)methylthiazolidine as colorless oil. This product was dissolved in methanol and to this solution was added 79 mg (0.681 mmol) of fumaric acid, and the mixture was concentrated under reduced pressure. The resulting residue was treated with acetonitrile to give crystalline. The crystalline was collected by filtration and dried in vacuum to give 271 mg of fumarate of the title Compound 14.

The following compounds were synthesized in accordance with the same procedures as described in Example 1.

Compound 1: 3-(6-chloro-3-pyridyl)methyl-2-[(6-chloro-3-pyridyl)methyl]iminothiazolidine;

Compound 2: 3-(6-chloro-3-pyridyl)methyl-2-[(6-chloro-3-pyridyl)-methyl]imino-3,4,5,6-tetrahydro-2H-1,3-oxazine;

Compound 5: 1-(6-chloro-3-pyridyl)methyl-2-[(6-chloro-3-pyridyl)methyl]imino-1,2-dihydropyrimidine;

Compound 8: 3-(6-chloro-3-pyridyl)methyl-2-[(6-chloro-3-pyridyl)methyl]imino-2,3-dihydrothiazole;

Compound 11: 3-(6-chloro-3-pyridyl)methyl-2-methylimino-thiazolidine;

Compound 13: 1-(6-chloro-3-pyridyl)methyl-2-imino-3-methyl-2,3-dihydroimidazole;

Compound 15: 3-(6-chloro-3-pyridyl)methyl-2-[2-(6-chloro-3-pyridyl)ethyl]iminothiazolidine.

Example 2

Synthesis by the Process 2

3-(6-Chloro-3-pyridyl)methyl-2-[(6-chloro-3-pyridyl) methyl]imino-4-methyl-2,3-dihydrothiazole [Compound 9]

A mixture of 228 mg (2 mmol) of 2-amino-4-methylthiazoline and 1.03 g (5 mmol) of 5-bromomethyl-2-chloropyridine in 30 ml of acetonitrile was heated for 8 hours at 90° C. under refluxing. Then, the reaction mixture was cooled to the room temperature, and the solvent was removed under reduced pressure. The resulting residue was mixed with dichloromethane and saturated sodium hydrogen carbonate aqueous solution, and the organic layer was separated. The water layer was extracted with dichloromethane, and combined organic layer was dried over magnesium sulfate. The solvent was removed under reduced pressure and the resulting residue was purified by silica gel 60 (Merck Co., Ltd.) column chromatography (eluent; dichloromethane:ethyl acetate=from 9:1 to 4:1) to give 600 mg (yield; 82.1%) of crude product as yellow oil. Then, this crude product was purified again by aminopropyl-coated silica gel (Chromatorex NH-type; Fuji Silysia Chemical Ltd.) column chromatography (eluent; dichloromethane), and the eluted product was crystallized by treatment with ether-isopropyl ether to give 310 mg (yield; 42.4%) of 3-(6-chloro-3-pyridyl)methyl-2-[(6-chloro-3-pyridyl)methyl]imino-4-methyl-2,3-dihydrothiazole as milky white crystalline. 200 mg (0.548 mmol) of this product was dissolved in methanol and to this solution was added 64 mg (0.551 mmol) of fumaric acid, and the mixture was concentrated under reduced pressure. The resulting residue was treated with acetonitrile to give crystalline. The crystalline was collected by filtration and dried in vacuum to give 213 mg of fumarate of the title Compound 9.

The following compounds were synthesized in accordance with the same procedures as described in Example 2.

Compound 3: 1-(6-chloro-3-pyridyl)methyl-[(6-chloro-3-pyridyl)methyl]imino-1,2,3,4,5,6-hexahydropyrimidine;

Compound 4: 1,3-bis[(6-chloro-3-pyridyl)methyl]-2-imino-1,2,3,4,5,6-hexahydropyrimidine;

Compound 6: 5-chloro-1-(6-chloro-3-pyridyl)methyl-2-[(6-chloro-3-pyridyl)methyl]imino-1,2-dihydropyridine;

Compound 7: 1-(6-chloro-3-pyridyl)methyl-2-[(6-chloro-3-pyridyl)methyl]imino-6-methylpiperidine;

Compound 10: 1,3-bis[(6-chloro-3-pyridyl)methyl]-2-imino-2,3-dihydroimidazole.

Example 3

Synthesis by the Process 3

3-(6-Chloro-3-pyridyl)methyl-2-phenylimino-2,3-dihydrothiazole [Compound 12]

A mixture of 176 mg (1 mmol) of 2-anilinothiazole and 227 mg (1.1 mmol) of 5-bromomethyl-2-chloropyridine in 10 ml of acetonitrile was heated for 15 hours at 90° C. under refluxing. Then, the reaction mixture was cooled to the room temperature, and the solvent was removed under reduced pressure. The resulting residue was mixed with dichloromethane and saturated sodium hydrogen carbonate aqueous solution, and the organic layer was separated. The water layer was extracted with dichloromethane, and combined organic layer was dried over magnesium sulfate. The solvent was removed under reduced pressure and the resulting residue was purified by silica gel 60 (Merck Co., Ltd.) column chromatography (eluent; dichloromethane:ethyl acetate=from 30:1 to 9:1) to give 57 mg (yield; 18.9%) of 3-(6-chloro-3-pyridyl)methyl-2-phenylimino-2,3-dihydrothiazole as yellow crystalline and 240 mg of mixture product of 3-(6-chloro-3-pyridyl)methyl-2-phenylimino-2,3-dihydrothiazole and 2-anilino-thiazole. Then, this crude mixture was purified by aminopropyl-coated silica gel (Chromatorex NH-type; Fuji Silysia Chemical Ltd.) column chromatography (eluent; hexane:ethyl acetate=5:1) to give 151 mg (yield; 50%) of 3-(6-chloro-3-pyridyl)methyl-2-phenylimino-2,3-dihydrothiazole. 208 mg (0.689 mmol) of the combined 3-(6-chloro-3-pyridyl)methyl-2-phenylimino-2,3-dihydro-thiazole was dissolved in methanol and to this solution was added 80 mg (0.689 mmol) of fumaric acid, and the mixture was concentrated under reduced pressure. The resulting residue was treated with acetonitrile to give crystalline. The crystalline was collected by filtration and dried in vacuum to give 192 mg (yeild; 45.9%) of fumarate of the title Compound 12.

The physiochemical data of the compound obtained by the above-mentioned examples are summarized in the following Table 1 to Table 3.

TABLE 1

| No. | Chemical Structure | Salt | Properties m.p. (° C.) solvent | Mass Spectrum found molecular formula | $^1$H-NMR(DMSO-d$_6$) |
|---|---|---|---|---|---|
| 1 | (structure) | fumarate | colorless cryst. 139–141° C. acetonitrile | m/z 353 = (M + H)$^+$ C$_{19}$H$_{18}$Cl$_2$N$_4$O$_4$S | 8.36(d, J=2.4Hz, 1H), 8.32(d, J=2.4Hz, 1H), 7.77 (dd, J=2.4, 8.2Hz, 1H), 7.73(dd, J=2.4, 8.2Hz, 1H), 7.47(d, J=8.2Hz, 1H), 7.44(d, J=8.2Hz, 1H), 6.63 (s, 2H), 4.57(s, 2H), 4.33(s, 2H), 3.50(t, J=6.8Hz, 2H), 3.26(t, J=6.8Hz, 2H) |
| 2 | (structure) | fumarate | colorless cryst. 128–129° C. acetone | m/z 351 = (M + H)$^+$ C$_{16}$H$_{16}$Cl$_2$N$_4$O$_3$ | 8.40(d, J=2.2Hz, 1H), 8.30(d, J=2.2Hz, 1H), 7.84 (dd, J=2.2, 8.2Hz, 1H), 7.71(dd, J=2.2, 8.2Hz, 1H), 7.50(d, J=8.2Hz, 1H), 7.43(d, J=8.2Hz, 1H), 6.54 (s, 2H), 4.63(s, 2H), 4.32(m, 4H), 3.30(m, 2H), 2.04(m, 2H) |
| 3 | (structure) | fumarate | pale yellow cryst. 177–179° C. acetone | m/z 350 = (M + H)$^+$ C$_{16}$H$_{17}$Cl$_2$N$_5$O$_2$ | 8.34(s, 1H), 8.31(s, 1H), 7.76(d, J=8.1Hz, 1H), 7.70(d, J=8.1Hz, 1H), 7.53(d, J=8.1Hz, 1H), 7.48 (d, J=8.1Hz, 1H), 6.33(s, 2H), 4.69(s, 2H), 4.41(s, 2H), 3.36(m, 2H), 3.28(m, 2H), 1.90(m, 2H) |
| 4 | (structure) | fumarate | pale yellow cryst. 196–197° C. acetonitrile | m/z 350 = (M + H)$^+$ C$_{16}$H$_{17}$Cl$_2$N$_5$O$_2$ | 8.38(d, J=2.5Hz, 1H), 7.80(dd, J=2.5, 8.2Hz, 2H), 7.56(d, J=8.2Hz, 2H), 6.32(s, 2H), 4.74(s, 4H), 3.37(t, J=5.8Hz, 4H), 1.96(t, J=5.8Hz, 2H) |
| 5 | (structure) | fumarate | milky white cryst. 178–182° C. acetonitrile | m/z 346 = (M + H)$^+$ C$_{16}$H$_{13}$Cl$_2$N$_5$ | 8.43(d, J=2.4Hz, 1H), 8.36(br, 1H), 8.26(d, J=2.4Hz, 1H), 8.20(br, 1H), 7.82(dd, J=2.4, 8.2Hz, 1H), 7.64(dd, J=2.4, 8.2Hz, 1H), 7.50(d, J=8.2Hz, 1H), 7.38(d, J=8.2Hz, 1H), 6.59(s, 2H), 6.21 (br, 1H), 5.14(s, 2H), 4.55(s, 2H) |

TABLE 2

| No. | Chemical Structure | Salt | Properties m.p.(°C.) solvent | Mass Spectrum found molecular formula | ¹H-NMR(DMSO-d₆) |
|---|---|---|---|---|---|
| 6 | (structure) | fumarate | pale red brownish cryst. 167–169° C. acetone | m/z 379 = (M + H)⁺ $C_{17}H_{13}Cl_3N_4$ | 8.40(d, J=2.4Hz, 1H), 8.29(d, J=2.4Hz, 1H), 8.08 (br, 1H), 7.78(dd, J=2.4, 8.2Hz, 1H), 7.66(dd, J=2.4, 8.2Hz, 1H), 7.47(d, J=8.2Hz, 1H), 7.40(d, J=8.2Hz, 1H), 7.28(br, 1H), 6.68(br, 1H), 6.21(s, 2H), 5.18(s, 2H), 4.33 (s, 2H) |
| 7 | (structure) | fumarate | pale yellow cryst. 178–180° C. acetone | m/z 363 = (M + H)⁺ $C_{18}H_{20}Cl_2N_4$ | 8.29(s, 1H), 8.25(s, 1H), 7.71(d, J=8.2Hz, 1H), 7.63(d, J=8.2Hz, 1H), 7.45(d, J=8.2Hz, 1H), 7.41 (d, J=8.2Hz, 1H), 6.48(s, 2H), 4.95(d, J=16.7Hz, 1H), 4.62(d, J=16.7Hz, 1H), 4.42(s, 2H), 3.63(m, 1H), 2.61(m, 2H), 1.87(m, 2H), 1.67(m, 2H), 1.19(d, J=6.3Hz, 3H) |
| 8 | (structure) | oxalate | colorless cryst. 112–116° C. acetone | m/z 351 = (M + H)⁺ $C_{15}H_{12}Cl_2N_4S$ | 8.40(d, J=2.4Hz, 1H), 8.37(d, J=2.4Hz, 1H), 7.78 (m, 2H), 7.52(d, J=8.2Hz, 1H), 7.46(d, J=8.2Hz, 1H), 7.28(d, J=4.7Hz, 1H), 6.45(d, J=4.7Hz, 1H), 5.07(s, 2H), 4.19(s, 2H) |
| 9 | (structure) | fumarate | milky white cryst. 145–148° C. acetone | m/z 365 = (M + H)⁺ $C_{16}H_{14}Cl_2N_4S$ | 8.32(d, J=2.4Hz, 2H), 7.73(dd, J=2.4, 8.2Hz, 1H), 7.68(dd, J=2.4, 8.2Hz, 1H), 7.48(d, J=8.2Hz, 1H), 7.42(d, J=8.2Hz, 1H), 6.63(s, 2H), 5.98(s, 1H), 5.06(s, 2H), 4.19(s, 2H), 2.09(s, 3H) |
| 10 | (structure) | fumarate | pale yellow cryst. 194–196° C. acetone | m/z 334 = (M + H)⁺ $C_{15}H_{13}Cl_2N_5$ | 8.43(s, 2H), 7.81(d, J=8.3Hz, 2H), 7.56(d, J=8.3Hz, 2H), 7.17(s, 2H), 6.35(s, 2H), 5.22(s, 4H) |

TABLE 3

| No | Chemical Structure | Salt | Properties m.p.(° C.) solvent | Mass Spectrum found molecular formula | ¹H-NMR(DMSO-d₆) |
|---|---|---|---|---|---|
| 11 | (structure: 2-methylimino-thiazolidine with (6-chloropyridin-3-yl)methyl) | fumarate | colorless cryst. 126–129° C. acetonitrile | m/z 242 = (M + H)⁺ $C_{10}H_{12}ClN_3S$ | 8.33(d, J=2.4Hz, 1H), 7.75(dd, J=2.4, 8.2Hz, 1H), 7.48(d, J=8.2Hz, 1H), 6.62(s, 2H), 4.49(s, 2H), 3.40(t, J=6.4Hz, 2H), 3.21(t, J=6.4Hz, 2H), 2.93(s, 3H) |
| 12 | (structure: 2-phenylimino-thiazoline with (6-chloropyridin-3-yl)methyl) | fumarate | colorless cryst. 181–187° C. acetonitrile | m/z 302 = (M + H)⁺ $C_{15}H_{12}Cl_2N_3S$ | 8.47(d, J=2.4Hz, 1H), 7.88(dd, J=2.4, 8.2Hz, 1H), 7.54(d, J=8.2Hz, 1H), 7.30(t, J=7.6Hz, 2H), 7.22(d, J=4.8Hz, 1H), 6.95(m, 3H), 6.27(d, J=4.8Hz, 1H), 5.08(s, 2H) |
| 13 | (structure: 2-imino-1-methyl-imidazoline with (6-chloropyridin-3-yl)methyl) | fumarate | pale yellow cryst. 146–148° C. acetone/AcOEt | m/z 223 = (M + H)⁺ $C_{10}H_{11}ClN_4$ | 8.43(d, J=2.2Hz, 1H), 7.81(dd, J=2.2, 8.3Hz, 1H), 7.56(d, J=8.3Hz, 1H), 7.13(d, J=2.4Hz, 1H), 7.06(d, J=2.4Hz, 1H), 6.47(s, 2H), 5.21(s, 2H), 3.46(s, 3H) |

TABLE 3-continued

| No | Chemical Structure | Salt | Properties m.p.(° C.) solvent | Mass Spectrum found molecular formula | $^1$H-NMR(DMSO-d$_6$) |
|---|---|---|---|---|---|
| 14 | (structure) | fumarate | colorless cryst. 140–141° C. acetonitrile | m/z 318 = (M + H)$^+$ C$_{16}$H$_{16}$ClN$_3$S | 8.37(d, J=1.6Hz, 1H), 7.79(dd, J=1.6, 8.2Hz, 1H), 7.47(d, J=8.2Hz, 1H), 7.27(m, 5H), 6.62(s, 2H), 4.58(s, 2H), 4.32(s, 2H), 3.48(t, J=6.7Hz, 2H), 3.25(t, J=6.7Hz, 2H) |
| 15 | (structure) | fumarate | colorless cryst. 102–105° C. acetonitrile | m/z 367 = (M + H)$^+$ C$_{16}$H$_{16}$Cl$_2$N$_4$S | 8.29(d, J=2.3Hz, 1H), 8.24(d, J=2.3Hz, 1H), 7.66 (m, 2H), 7.42(d, J=8.2Hz, 1H), 7.37(d, J=8.2Hz, 1H), 6.62(s, 2H), 4.47(s, 2H), 3.40(t, J=6.6Hz, 2H), 3.23(t, J=6.6Hz, 2H), 3.17(t, J=6.6Hz, 2H), 2.81(t, J=6.6Hz, 2H) |

The effect of the compounds (I) of the present invention was evaluated by the following biological experiments.

Biological Experiment 1
Binding Assays at α4β2 Subtype of Nicotinic Acetylcholine Receptors The affinity of the compounds of the present invention to α4β2 subunit of nicotinic acetylcholine receptors was performed by the following method, which was modified method described by Pabreza L. A., Dhawan S. & Kellar K. J., Mol. Pharm., 39, 9–12 (1990), and by Anderson D. J. & Arneric S. P., Eur. J. Pharm., 253, 261–267 (1994).

(1) Preparation of Rat Brain Membrane Containing α4β2 subtype of Nicotinic Acetylcholine Receptors Fischer-344 strain male rats (body weight: 200–240 g; 9 weeks old) obtained from Charles River Japan were used. Rats were housed in the breeding cage controlled of the room temperature at 23±1° C., and the humidity of 55±5% for 1 to 4 weeks. Rats (3 to 4 rats per a cage) were housed with lights on for 12 hours daily (from 7:00 to 19:00), and allowed free access to food and water.

Preparation of rat brain membrane containing α4β2 subtype of nicotinic acetylcholine receptors was performed as follow. That is, rat brains were isolated just after sacrificed by decapitation, washed with ice-cooled saline solution and then frozen at −80° C. with liquid nitrogen and stored till using. After thawing the frozen brain, the brain was homogenized in 10 volumes of buffer solution (50 mM of Tris-HCl, 120 mM of NaCl, 5 mM of KCl, 1 mM of $MgCl_2$, 2mM of $CaCl_2$; pH 7.4; 4° C.) using homogenizer (HG30, Hitachi Kohki Ltd.) for 30 seconds, and the homogenate were centrifuged under 1,000×G for 10 minutes at 4° C. The resulting supernatant was separated and the pellet was homogenized again with half volume of aforementioned prior buffer solution and centrifuged under the same conditions. Combined supernatant was further centrifuged under 40,000×G for 20 minutes at 4° C. The pellet was suspended in buffer solution and used for binding assays at receptors.

(2) Experiments of α4β2 Subtype of Nicotinic Acetylcholine Receptors Binding

Suspensions of membrane pellets containing 400–600 μg of protein were added to test tubes containing test compounds and [$^3$H]-cytisine (2 nM) in a final volume of 200 μl and incubated for 75 minutes in ice-cooled bath. The samples were isolated by vacuum filtration onto Whatman GF/B filters, which were prerinsed with 0.5% polyethylenimine just prior to sample filtration, using Brandel multi manifold cell harvester. The filters were rapidly washed with buffer solution (3×1 ml). The filters were counted in 3 ml of clearsol I (Nacalai Tesque Inc.). The determination of nonspecific binding was incubated in the presence of 10 μM (−)-nicotine.

The analyses of the experimental results were conducted by using the Accufit Competition Program (Beckman Ltd.).

Biological Experiment 2
Binding Assays at α1β1γδ Subtype of Nicotinic Acetylcholine Receptors The affinity of the compounds of the present invention to α1β1γδ subtype of nicotinic acetylcholine receptors was measured by the following method, which was modified method described by Garcha H. S., Thomas P., Spivak C. E., Wonnacott S. & Stolerman I. P., Psychopharmacology, 110, 347–354 (1993).

(1) Preparation of Rat Skeletal Muscles Containing α1β1γδ Subtype of Nicotinic Acetylcholine Receptors The substantially same animals described in the Biological Experiment 1 were used.

The isolation of α1β1γδ subtype of nicotinic acetylcholine receptors was performed as follow. That is, rat posterior skeletal muscles were isolated just after sacrificed by decapitation, washed with ice-cooled saline solution and then frozen at −80° C. with liquid nitrogen and stored till using. After thawing the frozen muscles, tissue was homogenized (40% w/v) with buffer solution [2.5 mM of sodium phosphate buffer (pH:7.2), 90 mM of NaCl, 2 mM of KCl, 1 mM of EDTA, 2 mM of benzamidine, 0.1 mM of benzethonium chloride, 0.1 mM of PMSF, 0.01% of sodium azide] in Waring blender [Waring blender 34BL97; WARING PRODUCTS DIVISION DYNAMICS CORPORATION OF AMERICA) for 60 seconds. The homogenate were centrifuged under 20,000×G for 60 minutes at 4° C. The supernatant was separated and the resulting pellet was added to the same buffer (1.5 ml/g wet weight), and homogenized under the same conditions. Triton X100 (2% w/v) was added and the mixture was stirred for 3 hours at 4° C. The centrifugation at 100,000×G for 60 minutes at 4° C. yielded the rat muscle extract as supernatant. This was stored at 4° C. for up to 4 weeks, and used for binding assays at receptors.

(2) Experiments of α1β1γδ Subtype of Nicotinic Acetylcholine Receptors Binding

Receptors binding experiments were performed as follow. That is, the extract of rat muscle containing 600–900 μg of protein was added to test tubes containing test compounds and incubated for 15 minutes at 37° C. Then, to this mixture was added 1 nM of [$^3$H]-α-bungarotoxin (α-Bgt) and further incubated for 2 hours. The samples were isolated by vacuum filtration onto Whatman GF/B filters, which were prerinsed with 0.5% polyethylenimine just prior to sample filtration, using Brandel multi manifold cell harvester. The filters were rapidly rinsed with washing solution (10 mM of $KH_2PO_4$, 150 mM of NaCl, pH 7.2, room temperature) (5×1 ml). The filters were counted in 3 ml of clearsol I (Nacalai Tesque Inc.). The determination of nonspecific binding was incubated in the presence of 1 μM α-Bgt. The solutions containing α-Bgt (labeled/non-labeled) were prepared by using buffer solution containing 0.25% of BSA. In the receptor binding experiments, said buffer solution was added for adjusting the final concentration of BSA to be 0.05%.

The analyses of the experimental results were conducted by as described in the Biological Experiment 1.

Table 4 shows the results of receptor binding studies of the compounds of the present invention and (−)-nicotine as compared compound.

TABLE 4

| | Affinities for receptors Ki | |
|---|---|---|
| Compound No. | α4β2*[1] | α1β1γδ**[2] |
| 1 | 16 nM | 420 μM |
| 2 | 22 nM | (95%, 56%) |
| 3 | 739 nM | (77%, 76%) |
| 4 | 475 nM | (49%, 30%) |
| 5 | (92%, 23%) | n.d. |
| 6 | (94%, 45%) | n.d. |
| 7 | (85%, 75%) | (85%, 52%) |
| 8 | 42 nM | 840 μM |
| 9 | 110 nM | (78%, 40%) |
| 10 | (89%, 46%) | n.d. |
| 11 | (93%, 18%) | n.d. |
| 12 | (109%, 84%) | (86%, 48%) |
| 13 | 15 nM | 320 μM |
| 14 | 123 nM | (64%, 20%) |

TABLE 4-continued

| | Affinities for receptors Ki | |
|---|---|---|
| Compound No. | α4β2*[1] | α1β1γδ**[2] |
| 15 | 86 nM | 479 μM |
| Nicotine | 1.6 nM | 182 μM |

*[1] Values indicated in a parenthesis show control % of [$^3$H]-cytisine binding at 1 μM and 10 μM of test compounds, respectively.
**[2] Values indicated in a parenthesis show control % of [$^3$H]-α-Bgt binding at 100 μM and 1,000 μM of test compounds.
n.d.: not determined.

Biological Experiment 3
Agonist Activities at Human α4β2 Subtype of Nicotinic Acetylcholine Receptors The agonist activities of the compounds of the present invention at human α4β2 subtype of nicotinic acetylcholine receptors was evaluated by the following method, which was modified method described by Papke R. L., Thinschmidt J. S., Moulton B. A., Meyer E. M. & Poirier A., Br. J. Pharmacol., 120, 429–438 (1997).

(1) Preparation of cRNA of Human α4β2 Subtype of Nicotinic Acetylcholine Receptors The cloning of human nicotinic acetylcholine receptor (hnACh-R) α4 cDNA and hnAC-R β2 cDNA were performed, in accordance with the conventional manners, by synthesizing the each DNA primers corresponding to the sequences of hnACh-R α4 cDNA and hnACh-R β2 cDNA [Monteggia L. M. et al., Gene, 155, 189–193 (1995); and Anand R., & Lindstrom J., Nucl. Acids Res., 18, 4272 (1990)], and obtained hnACh-R α4 cDNA and hnACh-R β2 cDNA by polymerase chain reaction (PCR), respectively. The obtained hnACh-R α4 cDNA and hnACh-R β2 cDNA were inserted to the cRNA expression vector (pSP64 polyA) having SP6 RNA promoter to construct hnACh-R α4/pSP64 polyA and hnACh-R β2/pSP64 polyA, respectively. After cutting from expression vector by restriction enzyme (EcoRI), transcription was performed by affecting SP6 RNA polymerase in the presence of cap analogues to obtain hnACh-R α4 cRNA and hnACh-R β2 cRNA, respectively.

(2) Expression of Human α4β2 Subtype Nicotinic Acetylcholine Receptors in *Xenopus* Oocytes Oocytes were purchased from Kitanihonseibustukyohzai Co., Ltd., which were already enucleated from *Xenopus laevis*, and used in this experiment.

The oocytes were treated with collagenase (Sigma type I; 1 mg/ml) in calcium-free modified Birth's solution (88 mM of NaCl, 1 mM of KCl, 2.4 mM of NaHCO$_3$, 0.82 mM of MgSO$_4$, 15 mM of HEPES, pH 7.6) under gently stirring at the room temperature for 90 minutes, and washed out the enzyme from the tissue. Then, oocytes were separated from ovarian follicle by tweezers, and isolated oocytes were placed in antibiotics containing modified Birth's solution (88 mM of NaCl, 1 mM of KCl, 2.4 mM of NaHCO$_3$, 0.82 mM of MgSO$_4$, 15 mM of HEPES, pH 7.6, and 0.1 v/v % of mixture solution containing of penicillin and streptomycin for incubation; Sigma Co.). Thus treated oocytes were injected with 50 nl of adjusted cRNAs (1.0 mg/ml), that is, each 50 ng of hnACh-R α4 cRNA and hnACh-R β2 cRNA per 1 oocyte by using automatic injector (NANOJECT; DRUMMOND SCIENTIFIC CO.), and further incubated for 4–14 days at 19° C. In oocytes, heterogeneous quintuple [(α4)$_2$(β2)$_3$] was composed by translation of injected cRNAs, and ion channel receptors were constructed on cell membrane.

(3) Agonist Activities at Human α4β2 Subtype of Nicotinic Acetylcholine Receptors The recordings of responses at human α4β2 subtype of nicotinic acetylcholine receptors by means of membrane potential holding method were performed as follow. That is, oocytes were placed in recording chamber with a total volume of 50 μl and were perfused with Ringer's solution (115 mM of NaCl, 2.5 mM of KCl, 1.8 mM of CaCl$_2$, 10 mM of HEPES, pH 7.3) containing atropine (1 μM) under flow rate of 1 ml/min. The membrane electric potentials were held at –50 mV by mean of the two electric membranes potential holding method (CEZ-1250; Nihon Kohden Co.). Test compounds were added to the perfusion solution, and recorded the peak strength of induced inward electric current. In order to normalize the responses of test compounds, the responses with acetylcholine (Ach) were recorded before and after application of the test compounds. Generally in the oocytes just after isolated, the response of internal muscarinic acetylcholine receptors, which is interior electric current caused by activation of calcium dependence chloride ion channels with increase of the intracellular calcium concentration by stimulation of receptors, is observed. However, the complete disappearances of these responses were confirmed when treated with collagenase or added 1 μM of atropine. Furthermore, the oocytes without injection of cRNAs showed no responses by Ach after treatment with collagenase. Therefore, the responses observed in oocytes with injection of hnACh-R α4 cRNA and hnACh-R β2 cRNA, i.e., the inward electric current induced by the intracellular influx of sodium ion according to the stimulation of receptors, would be the freshly observed responses of human α4β2 subtype nicotinic acetylcholine receptors.

Table 5 shows the results of the agonist activity test of compounds in the present invention and (–)-nicotine as reference compound.

TABLE 5

| Compound No. | Agonist effect |
|---|---|
| 1 | 6% |
| 2 | 27% |
| 8 | 11% |
| 13 | 5% |
| nicotine | 146% |

These date are shown in control % by response at 100 μM of the test compounds, in comparison with the response at 10 μM of acetylcholine (100%).

The following are Formulation Examples of the compounds (I) or pharmaceutically acceptable salt thereof according to the present invention Formulation Example 1 (Tablets)

| | |
|---|---|
| Compound 2 | 25 g |
| Lactose | 130 g |
| Crystalline cellulose | 20 g |
| Corn starch | 20 g |
| 3% aqueous solution of hydroxypropyl cellulose | 100 ml |
| Magnesium stearate | 2 g |

Compound 2, lactose, crystalline cellulose and corn starch were screened through a 60-mesh sieve, homogenized and charged into a kneader. A 3% aqueous solution of hydroxypropyl cellulose was added to the homogeneous mixture and the mixture was further kneaded. The product was granulated by a 16-mesh sieve, dried in air at 50° C., and again granulated by a 16-mesh sieve. Magnesium stearate was added to the granule and mixed again. The mixture was tabletted to produce tablets weighing 200 mg each and having an 8 mm diameter.

Formulation Example 2 (Capsules)

| | |
|---|---|
| Compound 2 | 25.0 g |
| Lactose | 125.0 g |
| Corn starch | 48.5 g |
| Magnesium stearate | 1.5 g |

The above components were finely pulverized and thoroughly mixed to produce a homogeneous mixture. The mixture was filled in gelatin capsules, 200 mg per capsule, to obtain capsules.

Formulation Example 3 (Injection)

The fumarate of Compound 2 was filled in an amount of 250 mg in a vial and mixed in situ with approximately 4–5 ml of injectable distilled water to make an injectable solution.

INDUSTRIAL APPLICABILITY

As described above, the compounds of the present invention possess high affinity for α4β2 nicotinic acetylcholine receptor of central nervous systems and activate said α4β2 nicotinic acetylcholine receptor as agonists or modulators. Therefore, the compounds of the present invention are useful for preventing or treating various kinds of diseases, which may be prevented or cured by activating nicotinic acetylcholine receptors.

Especially, the activators for α4β2 nicotinic acetylcholine receptors of the present invention are useful for preventing or treating various diseases such as dementia, senile dementia, presenile dementia, Alzheimer's disease, Parkinson's disease, cerebrovascular dementia, AIDS-related dementia, dementia in Down's syndrome, Tourette's syndrome, neurosis in chronic cerebral infarction, cerebral dysfunction caused by cerebral injury, anxiety, schizophrenia, depression, Huntington's disease, pain and so on.

What is claimed is:

1. Di-substituted iminoheterocyclic compound represented by formula (I):

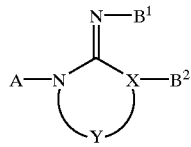

(I)

wherein:

A is a substituted alkyl group, wherein said substituent is a phenyl group, a substituted phenyl group, a heterocycic group, or a substituted heterocyclic group; or A is an optionally substituted heterocyclic group;

X is oxygen atom, and the group —Y—X— is —CH$_2$—CH$_2$—O— or —CH$_2$—CH$_2$—CH$_2$—O—; and B$^1$ is an optionally substituted alkyl group or an optionally substituted heterocyclic group;

or a pharmaceutically acceptable salt thereof.

2. A pharmaceutical composition comprising a di-substituted iminoheterocyclic compound represented by formula (I):

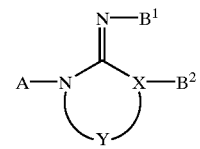

(I)

wherein:

A is a substituted alkyl group, wherein said substituent is a phenyl group, a substituted phenyl group, a heterocyclic group, or a substituted heterocyclic group; or an optionally substituted heterocyclic group;

X is oxygen atom, and the group —Y—X— is —CH$_2$—CH$_2$—O— or —CH$_2$—CH$_2$—CH$_2$—O—; and B$^1$ is an optionally substituted alkyl group or an optionally substituted heterocyclic group;

or a pharmaceutically acceptable salt thereof, as an active ingredient in combination with a pharmaceutically acceptable carrier.

3. The compound: 3-(6-chloro-3-pyridyl)methyl-2-[(6-chloro-3-pyridyl)methyl]imino-3,4,5,6-tetrahydro-2H-1,3-oxazine, or a pharmaceutically acceptable salt thereof.

4. A composition comprising a compound or a pharmaceutically acceptable salt thereof as claimed in claim 3, is an active ingredient, in combination with a pharmaceutically acceptable carrier.

5. A pharmaceutical composition comprising a compound or a pharmaceutically acceptable salt thereof as claimed in claim 1, as an active ingredient, in combination with a pharmaceutically acceptable carrier.

* * * * *